(12) United States Patent
Ladet

(10) Patent No.: US 8,968,733 B2
(45) Date of Patent: Mar. 3, 2015

(54) FUNCTIONALIZED SURGICAL ADHESIVES

(75) Inventor: Sebastien Ladet, Lyons (FR)

(73) Assignee: Sofradim Production (FR)

( * ) Notice: Subject to any disclaimer, the term of this patent is extended or adjusted under 35 U.S.C. 154(b) by 837 days.

(21) Appl. No.: 12/708,776

(22) Filed: Feb. 19, 2010

(65) Prior Publication Data

US 2010/0215659 A1 Aug. 26, 2010

Related U.S. Application Data

(60) Provisional application No. 61/154,378, filed on Feb. 21, 2009.

(51) Int. Cl.
| | |
|---|---|
| A61L 24/04 | (2006.01) |
| A61K 31/655 | (2006.01) |
| A61K 39/395 | (2006.01) |
| A61K 31/01 | (2006.01) |
| A61L 24/00 | (2006.01) |

(52) U.S. Cl.
CPC ............... *A61L 24/04* (2013.01); *A61L 24/001* (2013.01)
USPC .................. 424/133.1; 424/135.1; 424/130.1; 514/151; 514/762; 602/52

(58) Field of Classification Search
CPC ....... A61L 15/58; A61L 24/04; A61L 24/001; A61L 24/043; A61L 24/046; A61L 24/12; A61L 31/00; A61L 31/04; C08L 101/02; A61B 17/00491
See application file for complete search history.

(56) References Cited

U.S. PATENT DOCUMENTS

| | | | |
|---|---|---|---|
| 3,767,085 | A | 10/1973 | Cannon et al. |
| 4,359,049 | A | 11/1982 | Redl et al. |
| 4,361,055 | A | 11/1982 | Kinson |
| 4,538,920 | A | 9/1985 | Drake |
| 4,753,536 | A | 6/1988 | Spehar et al. |
| 4,839,345 | A | 6/1989 | Doi et al. |
| 4,857,403 | A | 8/1989 | De Lucca et al. |
| 4,874,368 | A | 10/1989 | Miller et al. |
| 4,880,662 | A | 11/1989 | Habrich et al. |
| 4,978,336 | A | 12/1990 | Capozzi et al. |
| 4,979,942 | A | 12/1990 | Wolf et al. |
| 5,368,563 | A | 11/1994 | Lonneman et al. |
| 5,372,585 | A | 12/1994 | Tiefenbrun et al. |
| 5,562,946 | A | 10/1996 | Fofonoff et al. |
| 5,578,662 | A | 11/1996 | Bennett et al. |
| 5,582,955 | A | 12/1996 | Keana et al. |
| 5,612,050 | A | 3/1997 | Rowe et al. |
| 5,911,942 | A | 6/1999 | Fofonoff et al. |
| 6,107,365 | A | 8/2000 | Bertozzi et al. |
| 6,107,453 | A | 8/2000 | Zuccato et al. |
| 6,451,032 | B1 | 9/2002 | Ory et al. |
| 6,527,749 | B1 | 3/2003 | Roby et al. |
| 6,534,611 | B1 | 3/2003 | Darling et al. |
| 6,552,103 | B1 | 4/2003 | Bertozzi et al. |
| 6,570,040 | B2 | 5/2003 | Saxon et al. |
| 6,576,000 | B2 | 6/2003 | Carrison |
| 6,881,766 | B2 | 4/2005 | Hain |
| 7,012,126 | B2 | 3/2006 | Matsuda et al. |
| 7,105,629 | B2 | 9/2006 | Matsuda et al. |
| 7,122,703 | B2 | 10/2006 | Saxon et al. |
| 7,144,976 | B2 | 12/2006 | Matsuda et al. |
| 7,172,877 | B2 | 2/2007 | Ting |
| 7,247,692 | B2 | 7/2007 | Laredo |
| 7,294,357 | B2 | 11/2007 | Roby |
| 7,371,719 | B2 | 5/2008 | Stupp et al. |
| 7,375,234 | B2 | 5/2008 | Sharpless et al. |
| 7,618,944 | B2 | 11/2009 | Breitenkamp et al. |
| 7,650,588 | B2 | 1/2010 | Ivansen |
| 7,667,012 | B2 | 2/2010 | Saxon et al. |
| 8,034,396 | B2 * | 10/2011 | Kapiamba et al. ........... 427/2.13 |
| 2002/0016003 | A1 | 2/2002 | Saxon et al. |
| 2002/0161170 | A1 | 10/2002 | Matsuda et al. |
| 2002/0169275 | A1 | 11/2002 | Matsuda et al. |
| 2002/0173616 | A1 | 11/2002 | Matsuda et al. |
| 2003/0100086 | A1 | 5/2003 | Yao et al. |
| 2003/0135238 | A1 | 7/2003 | Milbocker |
| 2003/0199084 | A1 | 10/2003 | Saxon et al. |

(Continued)

FOREIGN PATENT DOCUMENTS

| | | |
|---|---|---|
| EP | 0077098 A2 | 4/1983 |
| EP | 0328050 A2 | 8/1989 |

(Continued)

OTHER PUBLICATIONS

Q. Shi, et al., "The Immobilization of Proteins on Biodegradeable Polymer Fibers via Click Chemistry", Biomaterials, 29, (2008), pp. 1118-1126.

Jérôme, et al., "Recent Advances in the Synthesis of Aliphatic Polyesters Ring-Opening Polymerization", Advanced Drug Delivery Reviews, 60, (2008), pp. 1056-1076.

Zhang, et al., "2-Azido-2-deoxycellulose: Synthesis and 1, 3-Dipolar Cycloaddition", Helvetica Chimica Acta, vol. 91, pp. 608-617 (2008).

(Continued)

*Primary Examiner* — Shafiqul Haq

(57) ABSTRACT

A bioadherent composition includes a first mixture containing a plurality of reactive members of a specific binding pair, said reactive members being bound to a ligand capable of binding a receptor on biological tissue, and a second mixture containing a plurality of complementary reactive members of the specific binding pair, said complementary reactive members being bound to a ligand capable of binding a receptor on biological tissue, said reactive members capable of forming covalent bonds with said complementary reactive members via a reaction selected from Huisgen cycloaddition reactions, Diels-Alder reactions, and/or thiol-alkene reactions. A method for bonding biological tissue involves utilizing the bioadherent composition.

13 Claims, No Drawings

(56) References Cited

U.S. PATENT DOCUMENTS

| | | |
|---|---|---|
| 2003/0205454 A1 | 11/2003 | Hlavinka et al. |
| 2004/0170752 A1 | 9/2004 | Luthra et al. |
| 2004/0185053 A1 | 9/2004 | Govindan |
| 2004/0209317 A1 | 10/2004 | Ting |
| 2005/0038472 A1 | 2/2005 | Furst |
| 2005/0148032 A1 | 7/2005 | Saxon et al. |
| 2005/0222427 A1 | 10/2005 | Sharpless et al. |
| 2005/0233389 A1 | 10/2005 | Ting et al. |
| 2006/0018948 A1 | 1/2006 | Guire et al. |
| 2006/0085033 A1 | 4/2006 | Criscuolo et al. |
| 2006/0108393 A1 | 5/2006 | Heinrich et al. |
| 2006/0110782 A1 | 5/2006 | Bertozzi et al. |
| 2006/0147963 A1 | 7/2006 | Barone et al. |
| 2006/0193865 A1 | 8/2006 | Govindan |
| 2006/0228300 A1 | 10/2006 | Chang et al. |
| 2006/0228357 A1 | 10/2006 | Chang et al. |
| 2006/0240092 A1 | 10/2006 | Breitenkamp et al. |
| 2006/0276658 A1 | 12/2006 | Saxon et al. |
| 2007/0020620 A1 | 1/2007 | Finn et al. |
| 2007/0037964 A1 | 2/2007 | Saxon et al. |
| 2007/0060658 A1 | 3/2007 | Diaz et al. |
| 2007/0077564 A1 | 4/2007 | Roitman et al. |
| 2007/0086942 A1 | 4/2007 | Chang et al. |
| 2007/0087001 A1 | 4/2007 | Taylor et al. |
| 2007/0099251 A1 | 5/2007 | Zhang et al. |
| 2007/0140966 A1 | 6/2007 | Chang et al. |
| 2007/0178133 A1 | 8/2007 | Rolland |
| 2007/0178448 A1 | 8/2007 | Tsao et al. |
| 2007/0190597 A1 | 8/2007 | Agnew et al. |
| 2007/0244265 A1 | 10/2007 | Matyjaszewski et al. |
| 2007/0244296 A1 | 10/2007 | Tomalia et al. |
| 2007/0249014 A1 | 10/2007 | Agnew et al. |
| 2007/0254006 A1 | 11/2007 | Loose et al. |
| 2007/0258889 A1 | 11/2007 | Douglas et al. |
| 2007/0269369 A1 | 11/2007 | Gegg et al. |
| 2007/0272122 A1 | 11/2007 | Lahann et al. |
| 2007/0275387 A1 | 11/2007 | Ju |
| 2007/0298006 A1 | 12/2007 | Tomalia et al. |
| 2008/0015138 A1 | 1/2008 | Hamilton et al. |
| 2008/0035243 A1 | 2/2008 | Breitenkamp et al. |
| 2008/0038472 A1 | 2/2008 | Suzuki et al. |
| 2008/0045686 A1 | 2/2008 | Meagher et al. |
| 2008/0050731 A1 | 2/2008 | Agnew et al. |
| 2008/0051562 A1 | 2/2008 | Chaikof et al. |
| 2008/0121657 A1 | 5/2008 | Voegele et al. |
| 2008/0138317 A1 | 6/2008 | Fung |
| 2008/0160017 A1 | 7/2008 | Baker et al. |
| 2008/0166363 A1 | 7/2008 | Govindan et al. |
| 2008/0171067 A1 | 7/2008 | Govindan et al. |
| 2008/0187956 A1 | 8/2008 | Carrico et al. |
| 2008/0199736 A1 | 8/2008 | Gadeken et al. |
| 2008/0200628 A1 | 8/2008 | Gadeken et al. |
| 2008/0207913 A1 | 8/2008 | Breitenkamp et al. |
| 2008/0214436 A1 | 9/2008 | Yu et al. |
| 2008/0214801 A1 | 9/2008 | Saxon et al. |
| 2008/0214831 A1 | 9/2008 | Sharpless et al. |
| 2008/0221043 A1 | 9/2008 | Harth et al. |
| 2008/0241856 A1 | 10/2008 | Wong et al. |
| 2008/0241892 A1 | 10/2008 | Roitman et al. |
| 2008/0242171 A1 | 10/2008 | Huang et al. |
| 2008/0248126 A1 | 10/2008 | Cheng et al. |
| 2008/0267878 A1 | 10/2008 | Robillard et al. |
| 2008/0283572 A1 | 11/2008 | Boyden et al. |
| 2008/0311412 A1 | 12/2008 | Fokin et al. |
| 2009/0012457 A1 | 1/2009 | Childers et al. |
| 2009/0018646 A1 | 1/2009 | Zhao |
| 2009/0053139 A1 | 2/2009 | Shi et al. |
| 2009/0054619 A1 | 2/2009 | Baker et al. |
| 2009/0061010 A1 | 3/2009 | Zale et al. |
| 2009/0069561 A1 | 3/2009 | Fokin et al. |
| 2009/0082224 A1 | 3/2009 | Haddleton et al. |
| 2009/0124534 A1 | 5/2009 | Reineke et al. |
| 2009/0137424 A1 | 5/2009 | Tsao et al. |
| 2009/0181402 A1 | 7/2009 | Finn et al. |
| 2009/0182151 A1 | 7/2009 | Wu et al. |
| 2009/0202433 A1 | 8/2009 | Chang et al. |
| 2009/0214755 A1 | 8/2009 | Armani et al. |
| 2009/0220607 A1 | 9/2009 | Kiser et al. |
| 2009/0240030 A1 | 9/2009 | Ju et al. |
| 2009/0247651 A1 | 10/2009 | Kapiamba et al. |
| 2009/0250588 A1 | 10/2009 | Robeson et al. |
| 2009/0253609 A1 | 10/2009 | Fleury et al. |
| 2009/0259016 A1 | 10/2009 | Johnson et al. |
| 2009/0263468 A1 | 10/2009 | McAnulty et al. |
| 2009/0269277 A1 | 10/2009 | Chang et al. |
| 2009/0281250 A1 | 11/2009 | DeSimone et al. |
| 2009/0297609 A1 | 12/2009 | Shoichet et al. |
| 2009/0306310 A1 | 12/2009 | Wu et al. |
| 2009/0312363 A1 | 12/2009 | Bradner et al. |
| 2010/0011472 A1 | 1/2010 | Hugel et al. |
| 2010/0015046 A1 | 1/2010 | Govindan et al. |
| 2010/0021391 A1 | 1/2010 | Douglas et al. |
| 2010/0034862 A1 | 2/2010 | Laronde et al. |
| 2010/0047258 A1 | 2/2010 | Wang et al. |
| 2010/0048738 A1 | 2/2010 | Fleury et al. |
| 2010/0069578 A1 | 3/2010 | Faust et al. |
| 2010/0098640 A1 | 4/2010 | Cohen et al. |
| 2010/0121022 A1 | 5/2010 | Musa et al. |
| 2010/0159011 A1 | 6/2010 | Lian et al. |

FOREIGN PATENT DOCUMENTS

| | | |
|---|---|---|
| EP | 0490854 B1 | 9/1996 |
| EP | 1 757 314 | 2/2007 |
| EP | 1757314 A1 | 2/2007 |
| EP | 1975230 A1 | 1/2008 |
| EP | 2090592 A1 | 8/2009 |
| WO | 99/10019 | 3/1999 |
| WO | WO 99/10019 A2 | 3/1999 |
| WO | WO 00/62827 | 10/2000 |
| WO | WO 2004/054622 A1 | 7/2004 |
| WO | WO 2005/062854 A2 | 7/2005 |
| WO | WO 2005/079217 A2 | 9/2005 |
| WO | WO 2005/084180 A2 | 9/2005 |
| WO | WO 2005/084367 A2 | 9/2005 |
| WO | WO 2005/087818 A1 | 9/2005 |
| WO | WO 2005/113605 A1 | 12/2005 |
| WO | WO 2006/005046 A2 | 1/2006 |
| WO | WO 2006/012569 A1 | 2/2006 |
| WO | WO 2006/050262 A2 | 5/2006 |
| WO | WO 2006/065266 A2 | 6/2006 |
| WO | WO 2006/084202 A2 | 8/2006 |
| WO | WO 2006/086325 A2 | 8/2006 |
| WO | WO 2006/091894 A2 | 8/2006 |
| WO | WO 2006/107617 A2 | 10/2006 |
| WO | WO 2006/107786 A2 | 10/2006 |
| WO | WO 2006/107903 A2 | 10/2006 |
| WO | WO 2007/003054 A1 | 1/2007 |
| WO | WO 2007/035296 A2 | 3/2007 |
| WO | WO 2007/041394 A2 | 4/2007 |
| WO | WO 2007/041451 A2 | 4/2007 |
| WO | WO 2007/047668 A2 | 4/2007 |
| WO | WO 2008/004988 A1 | 1/2008 |
| WO | WO 2008/013618 A1 | 1/2008 |
| WO | WO 2008/031525 A1 | 3/2008 |
| WO | WO 2008/047057 A1 | 4/2008 |
| WO | WO 2008/075955 A2 | 6/2008 |
| WO | WO 2008/077406 A2 | 7/2008 |
| WO | WO 2008/108736 A1 | 9/2008 |
| WO | WO 2008/115694 A2 | 9/2008 |
| WO | WO 2008/120016 A1 | 10/2008 |
| WO | WO 2009/029242 A1 | 3/2009 |
| WO | WO 2009/064696 A1 | 5/2009 |
| WO | WO 2009/136853 A1 | 11/2009 |
| WO | WO 2009/140429 A2 | 11/2009 |

OTHER PUBLICATIONS

R. Riva, et al., "Contribution of "Click Chemisty" to the Synthesis of Antimicrobial Aliphatic Copolyester", Polymer 49, (2008), pp. 2023-2028.

Baskin, et al., "Copper Free Click Chemistry for Dynamic In Vivo Imaging", PNAS, vol. 104, No. 43, (Oct. 23, 2007), pp. 16793-16797.

Codelli, et al., "Second Generation Difluorinated Cyclooctynes for

(56) References Cited

OTHER PUBLICATIONS

Copper-Free Click Chemistry", J. Am. Chem. Soc., vol. 130, No. 34, (2008), pp. 11486-11493.
Sletton and Bertozzi, "A Hydrophilic Azacyclooctyne for Cu-free Click Chemistry", Org. Lett. (2008) 10(14), pp. 3097-3099.
Cazalis, et al., "Bioconjugate Chem.", 15 (2004), pp. 1005-1009.
Smith, et al., "Synthesis and Convenient Functionalization of Azide-labeled Diacyglycerol Analogues for Modular Access to Biologically Active Lipid Probes", Bioconjugate Chem, 19(9), (2008). pp. 1855-1863.
Haridas, et al., "Design and Synthesis of Triazole-based Peptidedendrimers" Tetrahedron Letters, vol. 48, (2007), pp. 4719-4722.
Raghavan, et al., "Chemical Probes for Profiling Fatty Acid-associated Proteins in Living Cells", Bioorg. Med. Chem. Lett., 18 (2008), pp. 5982-5986.
LeDevedec, et al., "Separation of Chitosan Oligomers by Immobilized Metal Affinity Chromatography", J. Chromatogr A., 2008, 1194(2), pp. 165-171.
Hartgerink, et al., "Pepti-damphiphile Nanofibers: A Versatile Scaffold for the Preparation of Self Assembling Materials", PNAS, 2002; 99(2), pp. 5133-5138.
Van Berkel, et al., Cem Bio Chem, 8, (2007), pp. 1504-1508.
Nottelet, et al., Biomaterials, 27, (2006), pp. 4948-4954.
Skierka, et al., "The Influence of Different Acids and Pepsin on the Extractability of Collagen From the Skin of Baltic Cod (*Gadus morhua*)", Food Chemisty, 105, (2007), pp. 1302-1306.
Eastoe, "The Amino Acid Composition of Mammalian Collagen and Gelatin", vol. 61, (1955), pp. 589-600.
Sicherl, et al., "Orthogonally Protected Sugar Diamino Acids as Building Blocks for Linear and Branched Oligosaccharide Mimetics", Angew. Chem. Int. Ed. 44, (2005), pp. 2096-2099.
Laughlin, et al., "In Vivo Imaging of Membrane-Associated Glycans in Developing Zebrafish", Science, 320, (2008), pp. 664-667.
Worch and Wittmann, "Unexpected Formation of Complex Bridged Tetrazoles via Intramolecular 1,3-dipolar Cycloaddition of 1,2-0-cyanoalkylidene Derivatives of 3-azido-3-deoxy-D-allose", Carbohydrate Research, 343, (2008), pp. 2118-2129.
Witczak et al., "A Click Chemistry Approach to Glycomimetics: Michael addition of 2,3,4,6-tetra-$O$-acetyl-1-thio-$\beta$-D-glucopyranose to 4-deoxy-1,2-$O$-isopropylident-L-*glycero*-pent-4-enopyranos-3-ulose-a convenient route to novel 4-deoxy-(1→5)-5-$C$-thiodisaccharides", Carbohydrate Research, 342, (2007), 1929-1933.
Marra, et al., "Validation of the Copper(I)-Catalyzed Azide-Alkyne Coupling in Ionic Liquids, Synthesis of a Triazole-Linked C-Disaccharide as a Case Study", J. Org. Chem (2008), 73(6), pp. 2458-2461.
Srinivasachari, et al., "Versatile Supramolecular pDNA Vehicles via "Click Polymerization" $\beta$-cyclodextrin with oligoethyleneamines", Biomaterials, 30, (2009), pp. 928-938.
Arora, et al., "A Novel Domino-click Approach for the Synthesis of Sugar Based Unsymmetrical bis-1,2,3-triazoles", Carbohydrate Research, 343, (2008), 139-144.
Chen, et al., "Synthesis of a $C_3$-symmetric (1→6)-$N$-acetyl-$\beta$-D-glucosamine Octadecasaccharide using Click Chemistry", Carbohydrate Research, 340, (2005), pp. 2476-2482.
Gouin, et al., "Multi-Mannosides Based on a Carbohydrate Scaffold: Synthesis, Force Field Development, Molecular Dynamics Studies, and Binding Affinities for Lectin Con A", J. Org. Chem., 2007, 72(24), pp. 9032-9045.
Srinivasachari, et al., "Effects of Trehalose Click Polymer Length on pDNA Complex Stability and Delivery Efficacy", Biomaterials, 28, (2007), pp. 2885-2898.
Godeau, et al., "Lipid-Conjugated Oligonucleotides via Click Chemistry" Efficiently Inhibit Hepatitis C Virus Translation, J. med. Chem., 2008, 51(15), pp. 4374-4376.
Zou et al., "Cu-free Cycloaddition for Identifying Catalytic Active Adenylation Domains of Nonribosomal Peptide Synthesis by phage display", Bioorganic & Medicinal Chemistry Letters, 18 (2008), pp. 5664-5667.
Cantel, et al., "Synthesis and Conformational Analysis of a Cyclic Peptide Obtained via $i$ to $i+4$ Intramolecular Side-chain to Side-chain Azide-Alkyne 1,3-Dipolar Cycloaddition" J. Org. Chem., 2008, 73 (15), pp. 5663-5674.
Dijk, et al., "Synthesis of Peptide-Based Polymers by Microwave-Assisted Cycloaddition Backbone Polymerization," Biomacro molecules, 2007, 8(2), pp. 327-330.
Köster, et al., "Spectroscopic and Electrochemical Studies of Ferroceryl Triazole Amino Acid and Peptide Bioconjugates Synthesized by Click Chemisty", Organometallics, 2008, 27(23) pp. 6326-6332.
Dijk, et al., "Synthesis and Characterization of Biodegradeable Peptide-Baed Polymers Prepared by Microwave-Assisted Click Chemistry", Biomacromolecules, 2008, 9(10), pp. 2834-2843.
Jiang, et al., "Amphiphilic PEG/alkyl-grafted comb polyactides", J. Polymer Science Part B: Polymer Physics, 45(22), pp. 5227-5236.
Ochs, et al., "Low-Fouling, Biofunctionalized, and Biodegradeable Click Capsules", Biomacromolecules, 2008, 9(12), pp. 3389-3396.
Beatty and Tirrell, "Two-color Labeling of Temporally Defined Protein Populations in Mammalian Cells", Bioorg. Med. Chem. Lett., 18 (2008), pp. 5995-5999.
Mammalian Cells, Bioorg. Med. Chem. Lett., 18 (2008), pp. 5995-5999.
Kolb, et al., "Click Chemistry: Diverse Chemical Function from a Few Good Reactions" vol. 40, Jun. 1, 2001, pp. 2004-2021.
International Search Report for PCT/IB10/000616 date of completion is Jan. 11, 2011 (3 pages).
Kolb, H C et al.: "Click Chemistry: Diverse Chemical Function from a Few Good Reactions", Angewandte Chemie. Interanation Edition, Wiley VCH Verlag, Weinheim LMKD-DOI: 10.1002/1521-3773(20010601)40:11<2004::AID-ANIE2004>3.0.CO; 2-5, vol. 40, Jun. 1, 2001, pp. 2004-2021, XP002506208, ISSN:1433-7851 p. 2008, left-hand column, line 31—right-hand column, line 15.

* cited by examiner

US 8,968,733 B2

FUNCTIONALIZED SURGICAL ADHESIVES

RELATED APPLICATIONS

This application claims the benefit of U.S. Provisional Patent Application No. 61/154,378 filed Feb. 21, 2009.

BACKGROUND

1. Technical Field

Adhesive modalities for repair of biological tissues.

2. Related Art

Techniques for repairing damaged or diseased tissue are widespread in medicine. Wound closure devices such as sutures, staples and other repair devices such as mesh or patch reinforcements are frequently used for repair. Surgical adhesives have been used to augment and, in some cases, replace sutures and staples in wound closure. Unfortunately, the use of such sutures or staples may increase the patient's discomfort and, in certain instances, there may be a risk of weakening thin or delicate tissue where they are attached. Surgical adhesives such as cyanoacrylates and fibrin glues have been used as fixatives in lieu of, or in addition to, suturing or stapling. However, fibrin adhesives can be difficult to prepare and store. Cyanoacrylates may cause irritation at the point of application and may not provide a sufficient degree of elasticity. In addition, surgical adhesives can tend to form a physical barrier between the item or items being attached to biological tissue, thus interfering with tissue ingrowth into the item when ingrowth is desired. There is a continuing need to generate improvements in tissue repair technology and advance the state of the art.

Click chemistry is a popular term for reliable reactions that make it possible for certain chemical building blocks to "click" together and form an irreversible linkage. See, e.g., US Pub. No. 2005/0222427. Copper-free click chemistry was recently developed by Bertozzi and colleagues using difluorinated cyclooctyne or DIFO, that reacts with azides rapidly at physiological temperatures without the need for a toxic catalyst. See, e.g., Baskin et al., Copper Free Click Chemistry for Dynamic In Vivo Imaging, PNAS, vol. 104, no. 43, 16793-16797 (Oct. 23, 2007). The critical reagent, a substituted cyclooctyne, possesses ring strain and electron-withdrawing fluorine substituents that together promote a [3+2] dipolar cycloaddition with azides. See also, US Pub. No. 2006/0110782 and Codelli et al., Second Generation Difluorinated Cyclooctynes for Copper-Free Click Chemistry, J. Am. Chem. Soc., vol. 130, no. 34, 11486-11493 (2008). Another suitable cyclooctyne is 6,7-dimethoxyazacyclooct-4-yne (DIMAC). See, Sletton and Bertozzi, A hydrophilic azacyclooctyne for Cu-free click chemistry, Org. Lett. (2008) 10 (14), 3097-3099. Other click chemistry reactions include Diels-Alder reactions, thiol-alkene reactions, and maleimide-thiol reactions.

SUMMARY

A method for bonding biological tissue is provided which includes providing a first mixture containing a plurality of reactive members of a specific binding pair, providing a second mixture containing a plurality of complementary reactive members of the specific binding pair, applying the first mixture to a first biological tissue surface to affix the reactive members to the first biological tissue surface, applying the second mixture to a second biological tissue surface to affix the complementary reactive members to the second biological tissue surface, wherein upon contact of the reactive members on the first biological tissue surface with the complimentary reactive members on the second biological tissue surface, covalent bonds are formed between the reactive members and the complementary reactive members, thus adhering the first biological tissue surface to the second biological tissue surface.

A bioadherent composition is provided which includes a first mixture containing a plurality of reactive members of a specific binding pair, said reactive members being bound to a ligand capable of binding a receptor on biological tissue, and a second mixture containing a plurality of complementary reactive members of the specific binding pair, said complementary reactive members being bound to a ligand capable of binding a receptor on biological tissue, said reactive members capable of forming covalent bonds with said complementary reactive members via a reaction selected from a Huisgen cycloaddition, a Diels-Alder reaction, and/or a thiol-alkene reaction.

A kit is provided which includes a first container containing a first mixture containing a plurality of reactive members of a specific binding pair, said reactive members being bound to a ligand capable of binding a receptor on biological tissue, a second container containing a second mixture containing a plurality of complementary reactive members of the specific binding pair, said complementary reactive members being bound to a ligand capable of binding a receptor on biological tissue, said reactive members capable of forming covalent bonds with said complementary reactive members via a reaction selected from Huisgen cycloaddition, Diels-Alder reactions, and/or a thiol-alkene reaction, and at least one dispenser for delivering the first mixture or the second mixture to the surface of biological tissue.

DETAILED DESCRIPTION

A surgical adhesive system is provided which covalently bonds reactive members of a specific binding pair to one another via click chemistry. Click chemistry refers to a collection of reactive members having a high chemical potential energy capable of producing highly selective, high yield reactions. The reactive members react to form extremely reliable molecular connections in most solvents, including physiologic fluids, and often do not interfere with other reagents and reactions. Examples of click chemistry reactions include Huisgen cycloaddition, Diels-Alder reactions, thiol-alkene reactions, and maleimide-thiol reactions.

Huisgen cycloaddition is the reaction of a dipolarophile with a 1,3-dipolar compound that leads to 5-membered (hetero)cycles. Examples of dipolarophiles are alkenes and alkynes and molecules that possess related heteroatom functional groups (such as carbonyls and nitriles). 1,3-Dipolar compounds contain one or more heteroatoms and can be described as having at least one mesomeric structure that represents a charged dipole. They include nitril oxides, azides, and diazoalkanes. Metal catalyzed click chemistry is an extremely efficient variant of the Huisgen 1,3-dipolar cycloaddition reaction between alkyl-aryl)-sulfonyl azides, C—N triple bonds and C—C triple bonds which is well-suited herein. The results of these reactions are 1,2 oxazoles, 1,2,3 triazoles or tetrazoles. For example, 1,2,3 triazoles are formed by a copper catalyzed Huisgen reaction between alkynes and alkyl/aryl azides. Metal catalyzed Huisgen reactions proceed at ambient temperature, are not sensitive to solvents, i.e., nonpolar, polar, semipolar, and are highly tolerant of functional groups. Non-metal Huisgen reactions (also referred to as strain promoted cycloaddition) involving use of a substituted cyclooctyne, which possesses ring strain and electron-withdrawing substituents such as fluorine, that together promote a [3+2] dipolar cycloaddition with azides are especially well-suited for use herein due to low toxicity as compared to the metal catalyzed reactions. Examples include DIFO and DIMAC. Reaction of the alkynes and azides is very specific and essentially inert against the chemical environment of biological tissues. One reaction scheme may be represented as:

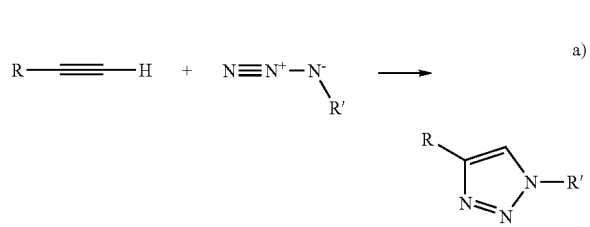

where R is a component of a first biological tissue and R' is a component of a second biological tissue. Alternatively, R' is a component of a first biological tissue and R is a component of a second biological tissue.

The Diels-Alder reaction combines a diene (a molecule with two alternating double bonds) and a dienophile (an alkene) to make rings and bicyclic compounds. Examples include:

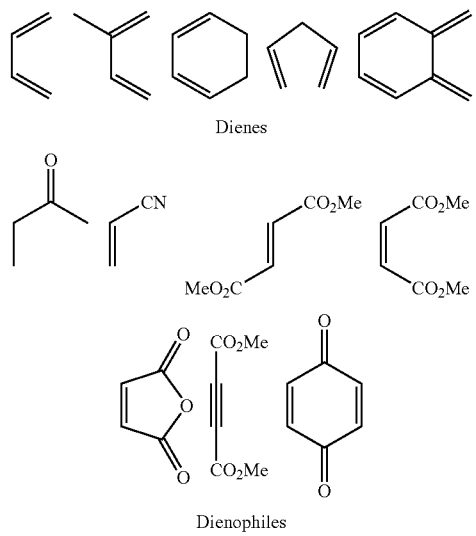

The thiol-alkene (thiol-ene) reaction is a hydrothiolation, i.e., addition of RS—H across a C=C bond. The thiol-ene reaction proceeds via a free-radical chain mechanism. Initiation occurs by radical formation upon UV excitation of a photoinitiator or the thiol itself. Thiol-ene systems form ground state charge transfer complexes and therefore photopolymerize even in the absence of initiators in reasonable polymerization times. However, the addition of UV light increases the speed at which the reaction proceeds. The wavelength of the light can be modulated as needed, depending upon the size and nature of the constituents attached to the thiol or alkene. A general thiol-ene coupling reaction mechanism is represented below:

Initiation
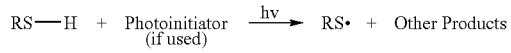
Propagation
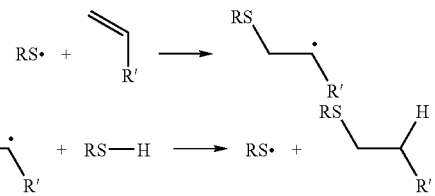
Termination
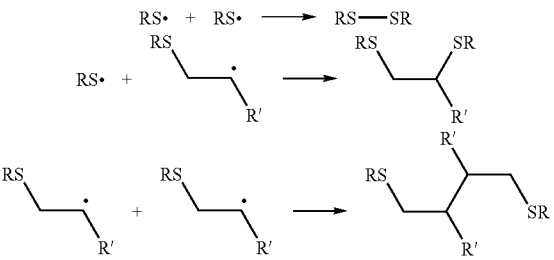

In accordance with the disclosure herein, a first mixture is provided with a plurality of reactive members of a specific binding pair attached to a plurality of ligands. The ligands may be the same or different. When the first mixture is contacted with a first biological tissue, the ligands bind to predetermined receptors on the tissue, thus affixing the reactive members of the specific binding pair to the tissue. A second mixture is provided with a plurality of complementary reactive members of the specific binding pair attached to a plurality of ligands. As above, the ligands may be the same or different. When the second mixture is contacted with a second biological tissue, the ligands bind to predetermined receptors on the second tissue, thus affixing the complementary reactive members of the specific binding pair to the second tissue. The first biological tissue is contacted with the second biological tissue so as to cause the reactive members on the first tissue to contact the complementary reactive members on the second tissue, and covalent attachment occurs between the members of the specific binding pair, thus adhering the first biological tissue to the second biological tissue.

In embodiments, the reactive members may be either a dipolarophile or a 1,3 dipolar compound depending on which complement is applied to the target tissue. For example, if a dipolarphile is located on the first tissue, the 1,3 dipolar compound will be located on the second tissue. If a dipolarphile is located on the second tissue, the 1,3 dipolar compound will be located on the first tissue. In embodiments, the Diels-Alder members of a specific binding pair may be either a diene and a dienophile depending on which complement is applied to the first tissue or the second tissue. For example, if a diene is located on the first tissue, the dienophile can be located on the second tissue. If a diene is located on the second tissue, the dienophile can be located on the first tissue. In embodiments, the thiol-ene members of a specific binding pair may be either a thiol and an alkene depending on which complement is applied to the first tissue or the second tissue. For example, if a thiol is located on the first tissue, the alkene can be located on the second tissue. If a thiol is located on the second tissue, the alkene can be located on the first tissue.

Biological tissue is provided with reactive members or complementary reactive members of a specific binding pair by conjugation to various components of tissue such as proteins, lipids, oligosaccharides, oligonucleotides, glycans, including glycosaminoglycans. In one embodiment, the reactive members or complementary reactive members are attached directly to components of the tissue. In another embodiment, the reactive members or complementary reactive members are attached to components of the tissue via a linker. The linker may include a ligand as described above and in more detail below. In either case, situating the reactive members or complementary reactive members on the tissue can be accomplished by suspending the reactive members or complementary reactive members in a solution or suspension and applying the solution or suspension to the tissue such that the reactive member or complementary reactive members binds to a target either directly or through a linker. The solution or suspension may be poured, sprayed or painted onto the tissue, whereupon the reactive members are incorporated into the tissue.

1,3-Dipolar compounds can be incorporated into proteins, lipids, oligosaccharides, oligonucleotides and glycans using, e.g., metabolic machinery, covalent inhibitors and enzymatic transfers. For example, an azido group, $N_3$, can be applied at the N-terminus of proteins or peptides using azidoacetyl chloride. See, e.g., Haridas, et al., Tetrahedron Letters 48 (2007) 4719-4722. The azido group is a nucleophilic group that will exchange with other nucleophilic groups, e.g., OH, $NH_2$ and halogens (Br, Cl, or I). $NaN_3$ is an azidizing agent which is capable of aziding proteins by simply contacting the proteins with a 10 times molar excess of $NaN_3$. A process for C-terminal azidization is described in Cazalis, et al., Bioconjugate Chem., 15 (2004) 1005-1009. Incubation of cells with peracetylated N-azidoacetylmannosamine provides cell surface glycans with azido sialic acid. See, e.g., Codelli et al., J. Amer. Chem. Soc., 130 (34) 11486-11493 (2008). Azido-tagged lipids are described in Smith, et al., Bioconjugate Chem., 19 (9), 1855-1863 (2008). PEGylation is a commonly used technique for adding groups to peptides and proteins and is suitable for use herein. For example, PEG may be covalently bound to amino acid residues via a reactive group. Reactive groups (as opposed to reactive members herein) are those to which an activated PEG molecule may be bound (e.g., a free amino or carboxyl group). For example, N-terminal amino acid residues and lysine (K) residues have a free amino group and C-terminal amino acid residues have a free carboxyl group. Sulfhydryl groups (e.g., as found on cysteine residues) may also be used as a reactive group for attaching PEG. In addition, enzyme-assisted methods for introducing activated groups (e.g., hydrazide, aldehyde, and aromatic-amino groups) specifically at the C-terminus of a polypeptide. Accordingly, PEG incorporating 1,3-dipolar compounds may be utilized herein. Those skilled in the art can utilize any known process for coupling a 1,3-dipolar compound into proteins, lipids, oligosaccharides, oligonucleotides and glycans.

Dipolarophile functionalized proteins and peptides can be synthesized by linking at the N-terminus with, for example, an alkyne (e.g., 3 butynyl chloroformate) in connection with a tripeptide (GlyGlyArg). See, Dirks, et al., supra. A suitable tripeptide herein is the well-known cell adhesion sequence RGD. It should be understood that, as used herein, "proteins" is intended to encompass peptides and polypeptides. In one embodiment, thiols on cysteines are functionalized with alkyne bearing maleimide. Id. Providing a C-terminal dipolarophile can be accomplished, e.g., by coupling with prop-argylamine using a cross-linking agent such as N-hydroxysuccinimide/DCC. See, e.g., Haridas, et al. supra. Terminal alkynes can be installed using metabolic building blocks such as alkynoic acids. Lipids may be functionalized with alkynes. For example, alkyne modified fatty acids can be generated by reaction of terminal alkynyl-alkyl bromide with trimethyl phosphine to yield a 16 carbon alkynyl-dimethylphosphonate. See, e.g., Raghavan et al., Bioorg. Med. Chem. Lett., 18 (2008) 5982-5986. As above, PEGylation may be used for adding dipolarophile groups to peptides and proteins and is suitable for use herein. Diels-Alder functionalities and thiolene functionalities are likewise attached to proteins, lipids, oligosaccharides, oligonucleotides and glycans.

As previously stated, the reactive members or complementary reactive members may be also attached to biological tissue via a linker. In certain embodiments, the linker includes a ligand which bears a reactive member or complementary reactive member. The ligand binds to a desired target on the tissue and thus provides a vehicle for transporting and indirectly binding the reactive member to the tissue. The ligand herein is any molecule or combination of molecules which demonstrates an affinity for a target. Examples of ligands include nucleic acid probes, antibodies, hapten conjugates, and cell adhesion peptides such as RGD. The mechanisms involved in obtaining and using such ligands are well-known. In embodiments, reactive members or complementary reactive members are incorporated into saccharides or polysaccharides and metabolically incorporated into cells. See, e.g., Baskin et al., supra.

Antibodies that specifically recognize antigens are useful in accordance with one embodiment herein. Antibodies which are conjugated to a reactive member or complementary reactive member are utilized to bind to proteins located on tissue. Monoclonal or polyclonal antibodies are raised against an antigen which can be any component of biological tissue and then purified using conventional techniques. The term "antibody" is intended to include whole antibodies, e.g., of any isotype (IgG, IgA, IgM, IgE, etc.), and to include fragments thereof which are also specifically reactive with a vertebrate, e.g., mammalian, protein. Antibodies may be fragmented using conventional techniques and the fragments screened for utility in the same manner as for whole antibodies. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The present disclosure includes polyclonal, monoclonal or other purified preparations of antibodies and recombinant antibodies.

After purification, the ligands, e.g., antibodies, nucleic acid probes, hapten conjugates and cell adhesion peptides are conjugated or linked to reactive members or complementary reactive members in the manners described above. In addition, reactive members or complementary reactive members can be linked to ligands by cross-linking procedures which, in accordance with the present invention, do not cause denaturing or misfolding of the ligands. The terms "linked" or "conjugated" as used herein are used interchangeably and are intended to include any or all of the mechanisms known in the art for coupling the reactive members or complementary reactive members to the ligand. For example, any chemical or enzymatic linkage known to those with skill in the art is contemplated including those which result from photoactivation and the like. Homofunctional and heterobifunctional cross linkers are all suitable. Reactive groups (distinguishable from reactive members or complementary reactive members herein) which can be cross-linked with a cross-linker include primary amines, sulfhydryls, carbonyls, carbohydrates and carboxylic acids.

Cross-linkers are conventionally available with varying lengths of spacer arms or bridges. Cross-linkers suitable for reacting with primary amines include homobifunctional cross-linkers such as imidoesters and N-hydroxysuccinimidyl (NHS) esters. Examples of imidoester cross-linkers include dimethyladipimidate, dimethylpimelimidate, and dimethylsuberimidate. Examples of NHS-ester cross-linkers include disuccinimidyl glutamate, disucciniminidyl suberate and bis(sulfosuccinimidyl) suberate. Accessible amine groups present on the N-termini of peptides react with NHS-esters to form amides. NHS-ester cross-linking reactions can be conducted in phosphate, bicarbonate/carbonate, HEPES and borate buffers. Other buffers can be used if they do not contain primary amines. The reaction of NHS-esters with primary amines should be conducted at a pH of between about 7 and about 9 and a temperature between about 4° C. and 30° C. for about 30 minutes to about 2 hours. The concentration of NHS-ester cross-linker can vary from about 0.1 to about 10 mM. NHS-esters are either hydrophilic or hydrophobic. Hydrophilic NHS-esters are reacted in aqueous solutions although DMSO may be included to achieve greater solubility. Hydrophobic NHS-esters are dissolved in a water miscible organic solvent and then added to the aqueous reaction mixture.

Sulfhydryl reactive cross-linkers include maleimides, alkyl halides, aryl halides and a-haloacyls which react with sulfhydryls to form thiol ether bonds and pyridyl disulfides which react with sulfhydryls to produce mixed disulfides. Sulfhydryl groups on peptides and proteins can be generated by techniques known to those with skill in the art, e.g., by reduction of disulfide bonds or addition by reaction with primary amines using 2-iminothiolane. Examples of maleimide cross-linkers include succinimidyl 4-{N-maleimido-methyl)cyclohexane-1-carboxylate and m-maleimidobenzoyl-N-hydroxysuccinimide ester. Examples of haloacetal cross-linkers include N-succinimidyl (4-iodoacetal) aminobenzoate and sulfosuccinimidyl (4-iodoacetal) aminobenzoate. Examples of pyridyl disulfide cross-linkers include 1,4-Di-[3'-2'-pyridyldithio(propionamido)butane] and N-succinimidyl-3-(2-pyridyldithio)-propionate.

Carboxyl groups are cross-linked to primary amines or hydrazides by using carbodiimides which result in formation of amide or hydrazone bonds. In this manner, carboxy-termini of peptides or proteins can be linked. Examples of carbodiimide cross-linkers include 1-ethyl-3-(3-dimethylaminopropyl)-carbodiimide hydrochloride and N,N$^1$-dicyclohexylcarbodiimide. Arylazide cross-linkers become reactive when exposed to ultraviolet radiation and form aryl nitrene. Examples of arylazide cross-linkers include azidobenzoyl hydrazide and N-5-azido-2 nitrobenzoyloxysuccinimide. Glyoxal cross linkers target the guanidyl portion of arginine. An example of a glyoxal cross-linker is p-azidophenyl glyoxal monohydrate.

Heterobifunctional cross-linkers which possess two or more different reactive groups are suitable for use herein. Examples include cross-linkers which are amine-reactive at one end and sulfhydryl-reactive at the other end such as 4-succinimidyl-oxycarbonyl-a-(2-pyridyldithio)-toluene, N-succinimidyl-3-(2-pyridyldithio)-propionate and the maleimide cross-linkers discussed above.

Attachment of reactive members to the biological tissue functionalizes the tissue such that upon exposure to their complementary reactive members which are situated on opposing tissue, they are activated and form a covalent bond, thus adhering the first tissue to the second tissue. In one embodiment, a linker between the product of the reactive members or complementary reactive members and the biological tissue is degradable, e.g., by hydrolysis or enzymatic action. In this manner, tissue bonding can be removable after a period of time. The degradable linkage may be chelates or chemically or enzymatically hydrolyzable or absorbable. Illustrative chemically hydrolyzable degradable linkages include polymers, copolymers and oligomers of glycolide, dl-lactide, l-lactide, caprolactone, dioxanone, and trimethylene carbonate. Illustrative enzymatically hydrolyzable biodegradable linkages include peptidic linkages cleavable by metalloproteinases and collagenases. Additional illustrative degradable linkages include polymers and copolymers of poly(hydroxy acid)s, poly(orthocarbonate)s, poly(anhydride)s, poly(lactone)s, poly(amino acid)s, poly(carbonate)s, poly(saccharide)s and poly(phosphonate)s. In certain embodiments, the degradable linkage may contain ester linkages. Some non-limiting examples include esters of succinic acid, glutaric acid, propionic acid, adipic acid, or amino acids, as well as carboxymethyl esters.

The ligand solution could be sterilized by any known method, e.g., irradiation, ethylene oxide, filtration in sterile conditions on a 0.22 um filter and the like.

Adhesives herein may be used in a variety of applications. In one embodiment, the first mixture is a liquid, functionalized with a plurality of reactive members of a binding pair, which is applied on surfaces of a first tissue in need of closure. Corresponding complementary second tissue which is intended to be bound to surfaces of the first tissue is treated with the complementary reactive member as described above. The first and second target tissues are treated by spraying, painting or pouring a solution or suspension containing the reactive members or complementary reactive members of a binding pair on to the respective tissue. Ligands associated with the reactive members bind to their predetermined targets on the tissue, thereby anchoring the reactive members and complementary reactive members on the tissue. The reactive members and the complementary reactive members of the specific binding pair react specifically together to form covalent bonds, providing adhesion between the first tissue and the second tissue. In certain embodiments, two opposing tissue surfaces are pretreated and functionalized, and then contacted to form bonds to both opposing surfaces. Some applications include using the present adhesive system to bind tissue together either as an adjunct to or as a replacement of sutures, staples, tapes and/or bandages.

A kit for a functionalized surgical adhesives herein includes a first container, which optionally functions as an applicator, containing a mixture which is a solution or suspension that includes a plurality of reactive members of a specific binding pair, the reactive members having a functionality that will adhere them to biological tissue upon contact. The kit includes a second container, which optionally functions as an applicator, containing a mixture which is a solution or suspension that includes a plurality of complementary reactive members of the specific binding pair, the complementary reactive members having a functionality that will adhere them to biological tissue upon contact. The kit may optionally include a container which contains a catalyst for causing the reactive members of a specific binding pair to bind with the complementary reactive members of the specific binding pair. The catalyst may be a metal. In embodiments, the container is a microwave or ultraviolet radiation generator.

It should be understood that variations can be made to the above embodiments that are with the purview of ordinary skill in the art. For example, other click chemistry reactions are suitable for use herein, e.g., staudinger reaction of phosphines with alkyl azides. Accordingly, those skilled in the art can envision modifications which are included within the scope of the claimed invention that are not expressly set forth herein.

What is claimed is:

1. A method for bonding biological tissue comprising: providing a first mixture containing a plurality of reactive members of a specific binding pair, the reactive members conjugated to a first ligand wherein the first ligand is capable of binding specifically to a first receptor on a first biological tissue surface; providing a second mixture containing a plurality of complementary reactive members of the specific binding pair, the complementary reactive members conjugated to a second ligand wherein the second ligand is capable of binding specifically to a second receptor on a second biological tissue surface; applying the first mixture to the first biological tissue surface to bind the first ligand to the first biological tissue surface and affix the reactive members to the first biological tissue surface; applying the second mixture to a second biological tissue surface to bind the second ligand to the second biological tissue surface and affix the complementary reactive members to the second biological tissue surface; wherein the members of the specific binding pair are alkynes and azides, and contacting the reactive members affixed to the first biological tissue surface with the complimentary reactive members affixed to the second biological tissue surface to form covalent bonds between the reactive members and the complementary reactive members, thus adhering the first biological tissue surface to the second biological tissue surface.

2. The method for bonding biological tissue according to claim 1 wherein the members of the specific binding pair bind to one another via a Huisgen cycloaddition reaction.

3. The method for bonding biological tissue according to claim 1 wherein the reactive member is an alkyne and the complementary reactive member is an azide.

4. The method for bonding biological tissue according to claim 1 wherein the reactive members is an azide and the complementary reactive member is an alkyne.

5. The method for bonding biological tissue according to claim 2 wherein the reaction is catalyzed by copper to activate the alkyne and the azide for [3+2] cycloaddition.

6. The method for bonding biological tissue according to claim 1 wherein the first ligand is selected from the group consisting of antibody, Fab, F(ab')$_2$, Fv, single chain antibody (SCA) and single complementary-determining region (CDR).

7. The method for bonding biological tissue according to claim 1 wherein the first ligand is an RGD linker.

8. The method for bonding biological tissue according to claim 1 wherein the second ligand is an RGD linker.

9. The method for bonding biological tissue according to claim 1 wherein the second ligand is selected from the group consisting of antibody, Fab, F(ab')$_2$, Fv, single chain antibody (SCA) and single complementary-determining region (CDR).

10. The method for bonding biological tissue according to claim 1 wherein the first ligand and the first biological tissue form a bond which is degradable by hydrolysis or enzymatic action.

11. The method for bonding biological tissue according to claim 1 wherein the first ligand binds to a receptor selected from the group consisting of peptides, oligosaccharides, oligonucleotides and lipids.

12. The method for bonding biological tissue according to claim 1 wherein the second ligand and the second biological tissue form a bond which is degradable by hydrolysis or enzymatic action.

13. The method for bonding biological tissue according to claim 1 wherein the second ligand binds to a receptor selected from the group consisting of peptides, oligosaccharides, oligonucleotides and lipids.

* * * * *